United States Patent
Cho et al.

(10) Patent No.: US 9,283,243 B2
(45) Date of Patent: Mar. 15, 2016

(54) CD36 INHIBITION TO CONTROL OBESITY AND INSULIN SENSITIVITY

(75) Inventors: Sunghee Cho, Hastings on Hudson, NY (US); Yi Bao, Chestnut Hill, MA (US); Eunhee Kim, White Plains, NY (US)

(73) Assignee: CORNELL UNIVERSITY CORNELL CENTER FOR TECHNOLOGY, ENTERPRISE & COMMERCIALIZATION ("CCTEC"), Ithaca, NY (US)

( * ) Notice: Subject to any disclaimer, the term of this patent is extended or adjusted under 35 U.S.C. 154(b) by 57 days.

(21) Appl. No.: 13/701,726

(22) PCT Filed: Jun. 1, 2011

(86) PCT No.: PCT/US2011/038714
§ 371 (c)(1),
(2), (4) Date: Jan. 17, 2013

(87) PCT Pub. No.: WO2011/153209
PCT Pub. Date: Dec. 8, 2011

(65) Prior Publication Data
US 2013/0116308 A1    May 9, 2013

Related U.S. Application Data

(60) Provisional application No. 61/350,274, filed on Jun. 1, 2010.

(51) Int. Cl.
| | |
|---|---|
| A61K 31/7088 | (2006.01) |
| A61K 31/343 | (2006.01) |
| A61K 31/19 | (2006.01) |
| A61K 31/4375 | (2006.01) |
| C07K 16/28 | (2006.01) |
| C12Q 1/68 | (2006.01) |
| A61K 39/00 | (2006.01) |

(52) U.S. Cl.
CPC .............. *A61K 31/7088* (2013.01); *A61K 31/19* (2013.01); *A61K 31/343* (2013.01); *A61K 31/4375* (2013.01); *C07K 16/2896* (2013.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 6,322,976 | B1 * | 11/2001 | Aitman et al. | 435/6.11 |
| 6,486,299 | B1 * | 11/2002 | Shimkets | 530/350 |
| 7,785,567 | B2 | 8/2010 | Ong et al. | |
| 8,603,971 | B2 * | 12/2013 | Szeto et al. | 514/6.9 |
| 8,742,082 | B2 * | 6/2014 | Tissot-Favre et al. | 536/23.1 |
| 2004/0202731 | A1 | 10/2004 | Gow et al. | |
| 2007/0248698 | A1 | 10/2007 | Kwak et al. | |
| 2008/0131534 | A1 | 6/2008 | Jungbauer et al. | |
| 2008/0146655 | A1 | 6/2008 | Yoo et al. | |
| 2011/0166226 | A1 * | 7/2011 | Cunha et al. | 514/548 |

FOREIGN PATENT DOCUMENTS

CN    1868546 A    11/2006

OTHER PUBLICATIONS

Koonen et al. Diabetes vol. 56:2863-2871, 2007.*
Wang et al. Journal of Biomolecular Screening vol. 15(3):239-250, Mar. 2010.*
Chinese Office Action corresponding to CN201180037754.9, dated Sep. 26, 2014 with English language translation.
Marleau, Sylvie, et al., "EP 80317, a ligand of the CD36 scavenger receptor, protects apolipoprotein E-deficient mice from developing atherosclerotic lesions"; The FASEB Journal, express article 10, Aug. 25, 2005.
Silverstein, Roy L., et al.,, "CD36, a Scavenger Receptor Involved in Immunity, Metabolism, Angiogenesis, and Behavior" ; Sci. Signal; 2(72): 2009.
Wang, S.B, et al., "Effect of salvionolilc acid A on vascular reactivity of streptoxotocin-induced diabetic rats"; Life Sciences 85 (2009) pp. 499-504.
Cheng, Suo-suo, et al., The correlation of CD36 with both fatty acid metabolism and insulin resistance; Int. J. Endocrinol Metab., 2010, 30, pp. 38-40.
Chinese Office Action dated Jun. 5, 2015 received in related CN 201180037754.9 together with an English language translation.

* cited by examiner

*Primary Examiner* — Sean McGarry
(74) *Attorney, Agent, or Firm* — Scully, Scott, Murphy & Presser, P.C.

(57) ABSTRACT

The disclosure relates to the therapeutic utility of CD36 antagonists to reduce body weight, inhibit fat accumulation and especially visceral fat accumulation, improve insulin sensitivity, lower blood glucose levels, and treat and prevent metabolic syndrome, pre-diabetes and diabetes, and lower plasma cholesterol levels and decrease fat deposit in the liver. CD36 antagonists, including SAB or its metabolites, such as RA and DSS, are useful for these purposes.

19 Claims, 5 Drawing Sheets

A.
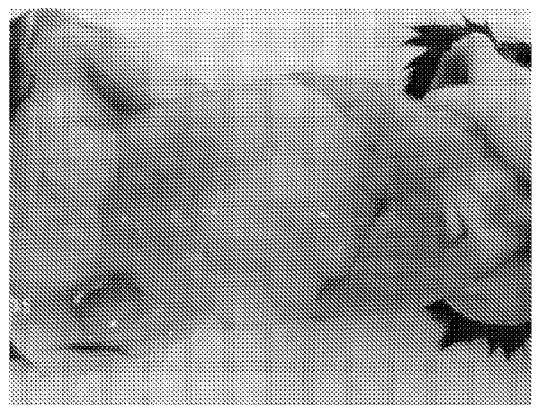
Veh
SAB
FIGURES 2A-2B
B.
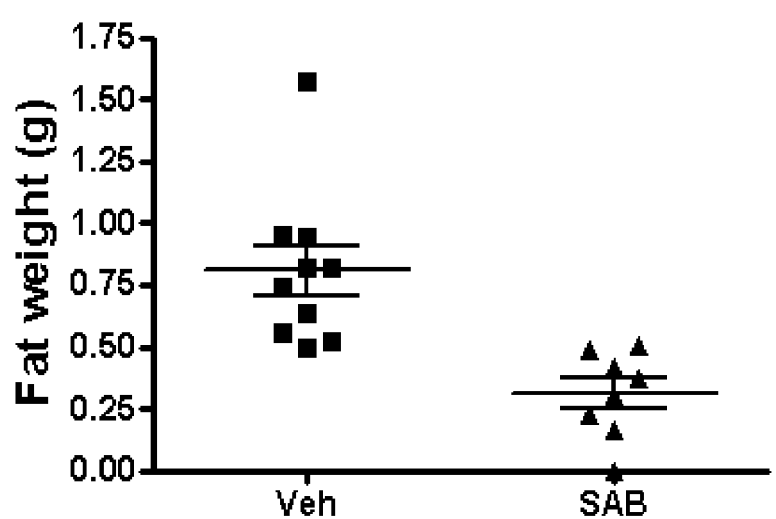

CD36 INHIBITION TO CONTROL OBESITY AND INSULIN SENSITIVITY

PRIORITY INFORMATION

This application claims priority to U.S. provisional application 61/350,274, filed Jun. 1, 2010, which is incorporated herein in its entirety.

GOVERNMENT FUNDING

This invention was made with Government support under Grant Numbers NHLBI RO1HL082511, NHLBI 3RO1HL082511-04S1, and NCRR UL1RR024996-03 awarded by the National Institutes of Health. The United States Government has certain rights in the invention.

BACKGROUND

CD36 is a multifunctional receptor that is expressed in various types of cells and tissues including brain microglia and astrocytes as well as monocytes/macrophages and adipocytes. CD36 recognizes many ligands including oxidized or modified low density lipoprotein (oxLDL, mLDL), long-chain fatty acids (LCFA), lipid and lipoprotein components of bacterial cell walls, thrombospondin (TSP) -1 and -2, fibrillar β-amyloid (fAβ), and dying cells (for detailed review see Febbraio, M., et al., *J Clin Invest* 108:785-791 (2001); Febbraio, M., et al., *Int J Biochem Cell Biol* 39:2012-2030 (2007)). Ligand recognition by CD36 initiates a signaling cascade that, on phagocytic cells such as macrophages, leads to phagocytosis of the ligand (such as lipids and fatty acids) and any other material the ligand may be bound to, such as cellular components, bacteria, etc. Internalization of oxLDL by CD36-expressing macrophages can lead to the formation of lipid-rich "foam cells" and atherosclerotic plaque, proinflammatory reactions, cytokine release, and/or production of reactive oxygen species, while internalization of β-amyloid peptide by CD36-expressing microglial cells may contribute to Alzheimer's disease (Silverstein R L et al, *Sci Signal* 2:re3 (2010)). CD36 is also expressed on taste bud cells and gut cells, and has been shown to be involved in preference for high-fat foods (Laugerette F et al., *J Clin Invest* 115:3177-3184 (2005)).

As consequence of its broad expression and ability to recognize many ligands, CD36 participates in the regulation of many processes including inflammation, angiogenesis, native immunity, clearance of foreign and native substances from the body, and lipid metabolism. Increased CD36 expression/function is associated with the pathology of atherosclerosis, stroke, and neurodegenerative diseases (Febbraio, M., et al., *J Clin Invest* 108:785-791(2001)).

Although its role in atherosclerotic lesion development is known, CD36's effects on body weight and insulin sensitivity are not clear. This lack of clarity results in part from the different genetic models used for study of metabolism and is compounded by multiple methods of removing or reducing CD36 in these models. A common atherosclerosis and lipid disease model organism is the Apolipoprotein E knockout ("ApoE KO") mouse, which lacks the ability to clear very low density lipoprotein particles from the body (Zhang et al., *Science* 258: 468-471, 1992). ApoE KO mice fed a normal diet develop hypercholesterolemia and atherosclerotic plaques, although they do not develop obesity in the absence of a high fat diet. ApoE/CD36 double knockout mice fed a high-fat diet exhibited a slightly increased body weight compared to ApoE KO mice fed a high fat diet in one study (Febbraio, M., et al., *J Clin Invest* 105:1049-1056 (2000)); however, another study found no difference in body weight between ApoE KO mice and ApoE KO mice treated with the CD36 antagonist EP80317 (Marleau, S., et al., *Faseb J* 19:1869-1871 (2005)).

Some evidence indicates that CD36 expression and/or function may be linked to diabetic conditions. However, CD36's role in insulin resistance is quite controversial. There is a potential interplay between impaired insulin sensitivity and the modulation of CD36 mediated inflammatory responses. In diabetic ob/ob mice, expression of macrophage CD36 increases in response to impaired insulin signaling, and administration of rosiglitazone (an insulin sensitizer) reduces CD36 expression in these mice (Liang C P, et al., *J Clin Invest* 113:764-773 (2004)). In addition, an association between glucose and CD36 expression has been identified (Sampson, M. J., et al., *Atherosclerosis* 167:129-134 (2003); Greenwalt, D. E., et al., *J Clin Invest* 9:1382-1388 (1995); Susztak, K., et al., *PLoS Med* 2, e45 (2005)). These findings indicate that CD36 is involved in impairment of insulin signaling. On the other hand, SHR rats that express a mutant CD36 are diabetic (Aitman, T. J., et al., *Nat Genet* 21:76-83 (1999)). CD36 KO mice that exhibit more proatherogenic profiles are not diabetic (Febbraio, M., et al., *J Biol Chem* 274:19055-19062 (1999)). These findings suggest a significant underlying complexity of CD36 in the regulation of carbohydrate/lipid metabolism, in which further research is needed.

SUMMARY

This disclosure is premised on the discovery of the therapeutic utility of inhibiting CD36 to reduce body weight, inhibit fat accumulation (especially visceral fat accumulation), improve insulin sensitivity, lower blood glucose levels, treat and prevent metabolic syndrome, pre-diabetes and diabetes, lower plasma cholesterol and lipid levels, and decrease fat deposit in the liver. CD36 antagonists, including SAB or its metabolites, such as RA and DSS, are useful for these purposes.

BRIEF DESCRIPTION OF THE DRAWINGS

FIG. 2A-2B. Visceral fat weight in high fat fed ApoE KO mice treated with SAB (100 mg/kg) for 8 weeks. 100 mg/kg SAB or vehicle (veh) was injected every other day by subcutaneous injection. n=8-10/group. (A), Reduction in abdominal fat was evident on physical inspection. (B), SAB reduced visceral fat weight from average=81 mg/animal to average=32 mg/animal. ***, p<0.001.

DETAILED DESCRIPTION

Figures 1A, 1B, 1C, 1D, 1E, 1F, 1G, 1H, 1I:
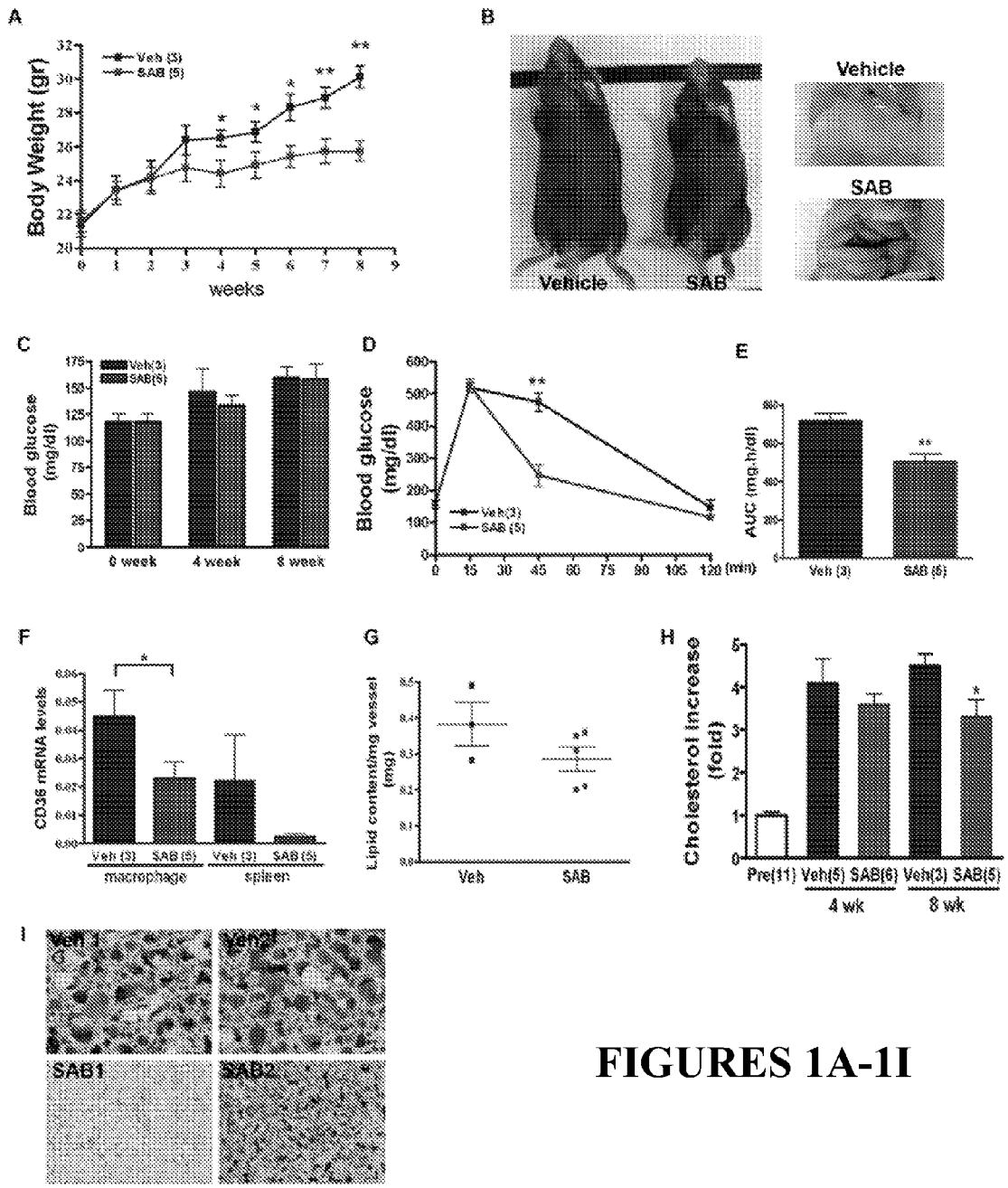
FIG. 1A-1I. In vivo effect of chronic SAB treatment on physiological responses. (A), Body weight changes in ApoE KO mice fed a high fat diet for 8 weeks in vehicle (Veh)- and salvianolic acid (SAB)-treated mice. (B), Pictures were taken at the end of 8 weeks of high fat diet. Note substantially reduced fat accumulation in SAB-treated mice. (C), Fasting blood glucose levels. (D), Glucose tolerance test. (E), Area under curve (AUC). (F), CD36 mRNA levels in peritoneal macrophages and spleen from vehicle and SAB treated mice. (G), Measurement of lipid content from blood vessels. Lipid extraction and determination was performed using published methods (Kim et al., 2008). (H), Fold increases of plasma cholesterol levels 4 and 8 weeks after high fat diet. (I), Oil red O staining in the liver of vehicle and SAB treated mice. Note that the numerous and large lipid droplets (dark grey/black areas) shown in the liver of vehicle-treated mice were profoundly reduced in the liver of the SAB treated mice. Number in parentheses indicates number of animals for the measurements.

In the following description, reference is made to the accompanying drawings that form a part hereof, and in which is shown by way of illustration specific embodiments that can be practiced. These embodiments are described in detail to enable those skilled in the art to practice the invention, and it is to be understood that other embodiments can be utilized and that logical changes can be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

It has been unexpectedly discovered in accordance with this disclosure that a CD36 antagonist can reduce body weight and improved insulin sensitivity. The results described in the Examples below demonstrate a dramatic reduction of body weight in ApoE KO mice that received SAB in conjunction with a high fat diet. In addition to the effect on body weight, it was also observed that 8 weeks of SAB treatment in hyperlipidemic ApoE KO improved insulin sensitivity. These findings are consistent with a therapeutic utility of inhibiting CD36 to reduce body weight, inhibit fat accumulation, lower blood glucose levels, improve insulin sensitivity, treat or prevent pre-diabetes and diabetes, especially Type II Diabetes, lower plasma cholesterol levels and decrease fat deposit in the liver, in subjects in need thereof. SAB or its metabolites, including RA and DSS, as well as other CD36 antagonists, are useful for these purposes.

CD36 Antagonists. A "CD36 antagonist", as used herein, refers to an isolated compound that inhibits CD36 activity or function. For example, a compound can act as a CD36 antagonist by inhibiting, reducing or eliminating CD36, or preventing binding CD36 to its ligands, or preventing interaction of CD36 with other proteins, resulting in an inhibition of a CD36-mediated function or signaling.

CD 36 is known to recognize and bind to ligands, including oxidized or modified low density lipoprotein (oxLDL, mLDL); long-chain fatty acids (LCFA); lipid and lipoprotein components of bacterial cell walls; thrombospondin (TSP) -1 and -2 and molecules with a peptide domain containing a thrombospondin type 1 repeat (TSR); fibrillar β-amyloid (fAβ); dying/apoptotic cells; glycated proteins; and phospholipids.

CD36 is also known to interact with other cellular proteins, such as other membrane proteins and signaling proteins such as Src family kinases and MAPK kinases that orchestrate downstream signaling events; and induction of cellular responses such as cell signaling, internalization or phagocytosis of ligand and ligand-bound materials such as endogenous substances (e.g., oxLDLs or infected/apoptotic cells) and foreign substances (e.g., bacteria or other parasites).

CD36 mediates an array of cellular and physiological events through ligand binding and cellular interactions, including inflammatory responses (e.g., induction of cytokine release, inhibition of macrophage migration, activation of NF-κB), angiogenesis (e.g., inhibition of proangiogenic signals), tissue infarction, foam cell formation (e.g., promotion of foam cell formation), atherosclerosis (e.g., promotion of atherosclerotic plaque formation), gut fatty acid absorption (e.g., binding of CD36-expressing gut cells to fatty acids and initiation of fatty acid internalization), and taste preference (e.g., binding of taste-bud cell CD36 to lipids/fatty acids and initiation of a signal cascade leading to preference for high-fat foods).

CD36 activities are also believed to promote glucose intolerance; insulin resistance; fat deposit formation, particularly visceral/abdominal fat deposits; excess body weight and weight gain; elevated plasma cholesterol; and increased lipid content in macrophages, aeorta and extended blood vessels.

As disclosed herein, CD36 antagonists include, but are not limited to, a small molecule, an aptamer, a small interfering RNA molecule, an antisense molecule, or an antibody.

In one aspect of the disclosure, the antagonist of CD36 activity is an aptamer, which is an oligo nucleic acid or peptide (or polypeptide) molecule that binds a specific target molecule. Aptamers can be synthesized specifically or selected from a pool using various screening methods known in the art, for example a yeast two-hybrid system.

In another aspect of the disclosure, the antagonist is an antibody. For example, the CD36 antagonist antibody clone FA6-152 can be obtained from Immunotech (Beckman Coulter, Fullerton, Calif.).

In still another aspect of the disclosure, the CD36 antagonist is a small interfering RNA (siRNA) molecule. Examples of suitable siRNA molecules include those described in the examples below.

In one aspect, the antagonist of CD36 activity is a small molecule. In this context, the term "small molecule" refers to small organic compounds, such as heterocycles, peptides, saccharides, steroids, and the like. The small molecule modulators preferably have a molecular weight of less than about 1500 Daltons, 1000 Daltons, 800 Daltons, or even less than about 500 Daltons. The compounds may be modified to enhance efficacy, stability, pharmaceutical compatibility, and the like.

Candidate modulator compounds from libraries of synthetic or natural compounds can be screened by methods known in the art (see Chinese patent number ZL200510072269.1, Publication No: CN1868546, and Chinese patent application number 200910147634.9, each hereby incorporated in its entirety by reference). Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds can be further modified through conventional chemical and biochemical techniques.

The use of high throughput screening has allowed the identification of compounds that potently antagonize CD36 in vitro. Following isolation of CD36 antagonists by in vitro testing, experiments can be conducted to test the efficacy in vivo. For example, a lead compound, salvianolic acid B (SAB; CAS Registry Number 115939-25-8), has been identified as a CD36 antagonist in a high throughput screen.

The structure of SAB is:

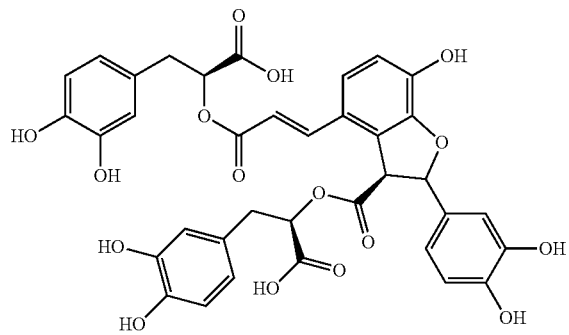 [SMILES: O=C(/C=C/c1ccc(O)c2c1[C@H](C(=O)O[C@H](Cc1ccc(O)c(O)c1)C(=O)O)C(c1ccc(O)c(O)c1)O2)O[C@@H](Cc1ccc(O)c(O)c1)C(=O)O]

SAB metabolizes into rosmarinic acid (RA: CAS Registry number 20283-92-5) and sodium danshensu (DSS; CAS Registry number 67920-52-9).

The structure of RA is:

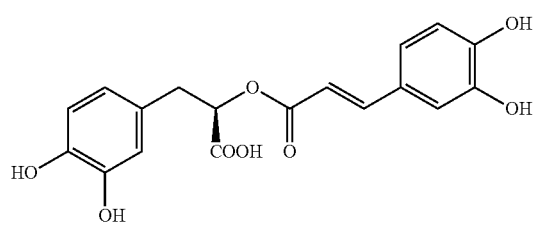 [SMILES: O=C(/C=C/c1ccc(O)c(O)c1)O[C@H](Cc1ccc(O)c(O)c1)C(=O)O]

The structure of DSS is:

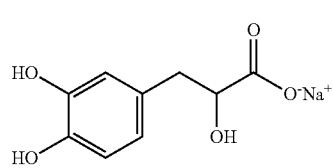

In certain embodiments, the small molecule antagonist of CD36 activity can be selected from SAB, its metabolites RA and DSS (as described above), and derivatives thereof. SAB or its metabolites can be derivatized, for example, as esters, ethers, oximes, hydrazones, hydroxyamines, carbamate esters, alkoxyesters, or carbonate esters in 1-3 enzymatic steps, or PEG derivatives.

Other small molecule antagonists of CD36 have been identified through high-throughput screening, for example the following two structures, 3-cinnamoyl indole, and 13 pentyl berberine (Xu, Y et al., Anal Biochem 400(2): 207-212 (2010)):

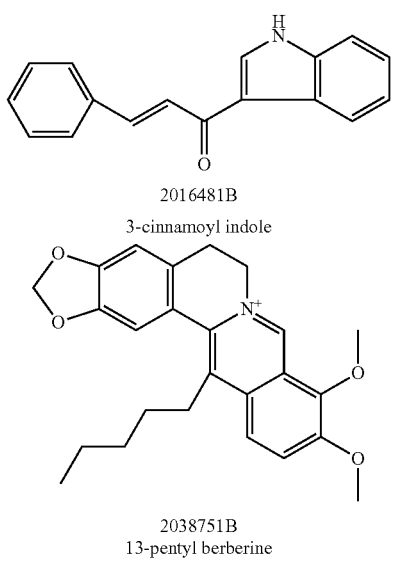

Another example of a small molecule CD36 antagonist is hexarelin, a member of the hexapeptide growth hormone-releasing peptides (GHRPs) family that possesses growth hormone releasing activity and binds to CD36 receptors (Demers A et al., Biochem J. 382(Pt 2):417-24(2004)). Hexarelin blocks CD36-mediated uptake of oxLDLs through binding site competition, since the binding domain of hexarelin on CD36 overlaps that of oxLDLs (Demers A et al., Biochem J. 382(Pt 2):417-24(2004)).

Other antagonists against scavenger receptors include synthetically engineered nanoblockers. After self-assembling into 15-20 nm ligand units, these nanoparticles block the major scavenger receptors from oxLDLs uptake and thus prevent formation of foam cells (Chnari E, et al., Biomacromolecules. 7(6):1796-805(2006)).

Statins or antioxidants can modulate CD36 expression or its downstream effects. Some statins and the antioxidant α-tocopherol can reduce expression of CD36 and the uptake of oxLDLs into macrophages (Venugopal SK, et al., Atherosclerosis. 175(2):213-20 (2004), Ricciarelli R, et al., Circulation 102: 82-87 (2000), Fuhrman B, et al., Atherosclerosis 164(1): 179-85 (2002)).

Another class of antioxidants is SS peptides. The SS peptides SS31 has been shown to attenuate ischemia-induced GSH depletion in the cortex and reduced infarct size. This attenuation has been observed to be abrogated in CD36 knock-out mice, indicating that the protective effect of SS31 occurs via down regulating CD36-mediated pathways (Cho S, et al., J Biol Chem. 282(7):4634-42 (2007)).

Treatment with CD36 antagonists. As used herein, the term "treatment" refers to effective inhibition of the activity of CD36 so as to slow down the progression, or ameliorate the symptoms, of the condition for which treatment is desired. For example, treatment of obesity with an effective amount of a CD36 antagonist as disclosed herein can lead to loss of body weight, or reducing or retarding the amount of gain of body weight. Similarly, treatment of excess fat, particularly abdominal/visceral fat deposits or liver fat deposits, with an effective amount of a CD36 antagonist can lead to reduced fat deposits or prevention of further fat deposits. In addition, treatment of insulin resistance and elevated blood glucose levels with an effective amount of a CD36 antagonist can lead to improved insulin sensitivity and reduced blood glucose levels. Further, treatment of diabetes or pre-diabetes with an effective amount of a CD36 antagonist can lead to amelioration of diabetic or pre-diabetic symptoms. Also, treatment of metabolic syndrome with an effective amount of a CD36 antagonist can lead to improvement of metabolic disease symptoms.

Subjects: The subject who is in need of treatment with a CD36 antagonist can be any animal, including a human. The subject is generally diagnosed with the condition by skilled artisans, such as a medical practitioner.

The methods of the invention described herein can be employed for subjects of any species, gender, age, ethnic population, or genotype. Accordingly, the term patient includes males and females, and it includes pre-adults, transition age patients, and adults.

Examples of human ethnic populations include Caucasians, Asians, Hispanics, Africans, African Americans, Native Americans, Semites, and Pacific Islanders. The methods of the invention can be more appropriate for some ethnic populations such as Caucasians, especially northern European populations, as well as Asian populations.

The term subject also includes patients of any genotype or phenotype as long as they are in need of the invention, as described above. In addition, the patient can have the genotype or phenotype for any hair color, eye color, skin color or any combination thereof.

The term subject includes a patient of any body height, body weight, or any organ or body part size or shape.

Conditions in which a subject will be in need of treatment with a CD36 antagonist include a condition of being overweight or obese. Obesity is a medical condition in which excess body fat has accumulated to the extent that it can have an adverse effect on health, leading to reduced life expectancy and/or increased health problems. Body mass index (BMI), a measurement which compares weight and height, defines people as overweight (pre-obese) when their BMI is between 25 kg/m$^2$ and 30 kg/m$^2$, and obese when it is greater than 30 kg/m$^2$. Inhibiting CD36 can treat or prevent obesity and the condition of being overweight by causing weight reduction and inhibiting accumulation of fat. The fat that is inhibited from accumulating can be visceral fat, subcutaneous fat, intramuscular fat, or other fat. The fat can be comprised of white adipose tissue and/or brown adipose tissue.

Conditions in which a subject will be in need of the treatment disclosed herein also include a condition of having abnormally high blood glucose levels, being insensitive to insulin or insulin resistant, being pre-diabetic or being diabetic, or having metabolic syndrome.

"Pre-diabetes" is a condition many people enter prior to developing type 2 diabetes. Pre-diabetic patients almost always have blood glucose levels that are higher than normal but not yet high enough to be diagnosed as diabetes. There are 57 million people in the United States who have pre-diabetes.

Recent research has shown that some long-term damage to the body, especially the heart and circulatory system, can already be occurring during pre-diabetes. Currently, there are three tests a doctor can use to determine whether a patient has pre-diabetes: the A1C test, the fasting plasma glucose test (FPG) and/or the oral glucose tolerance test (OGTT). The blood glucose levels measured after these tests determine whether a patient has a normal metabolism, or whether a patient has pre-diabetes or diabetes. If a patient's blood glucose level is abnormal following the FPG, the patient has impaired fasting glucose (IFG); if the patient's blood glucose level is abnormal following the OGTT, the patient has impaired glucose tolerance (IGT). Both are also known as pre-diabetes. The blood glucose level that is "abnormal" in these tests is known in the art, for example, IGT can be defined as an elevated 2-hour plasma glucose concentration (between 140 and 199 mg/dl) after a 75-g glucose load in an OGTT in the presence of an FPG concentration <126 mg/dl (Nathan, D. M., et al., *Diabetes Care* 30:753-759, 2007).

Diabetes mellitus, often simply referred to as diabetes, is a condition in which a person has a high blood sugar (glucose) level, either because the body doesn't produce enough insulin, or because body cells don't properly respond to the insulin that is produced. Diabetes can be diagnosed, for example, from an OGTT as a 2-hour plasma glucose concentration of greater than or equal to 200 mg/dl. Insulin is a hormone produced in the pancreas that enables body cells to absorb glucose, to turn into energy. If the body cells do not absorb the glucose, the glucose accumulates in the blood (hyperglycemia), leading to vascular, nerve, and other complications. There are many types of diabetes, the most common of which are:

Type 1 diabetes: results from the body's failure to produce insulin, and presently requires the person to inject insulin.

Type 2 diabetes: results from insulin resistance, a condition in which cells fail to use insulin properly, sometimes combined with an absolute insulin deficiency.

Gestational diabetes: is when pregnant women, who have never had diabetes before, have a high blood glucose level during pregnancy. It can precede development of type 2 DM.

Methods to test insulin sensitivity, and diagnose insulin resistance, are known in the art. Common tests for insulin sensitivity include the hyperinsulinemic-euglycemic clamp technique, the insulin sensitivity test (IST), and the insulin tolerance test (ITT). These tests measure plasma glucose concentrations in response to intravenous insulin infusion. Blood glucose concentrations indicating normal insulin sensitivity in a general population range from 0.026 to 0.085 mmol/L/minute for persons with a BMI below 30 kg/m$^2$, and from 0.012 to 0.017 mmol/L/minute for obese subjects (BMI>30 kg/m$^2$; McAuley K. A., et al., *Diabetes Care* 24:460-464 (2001)). A modified OGTT that uses a 75- or 100-g glucose load and measures glucose and insulin at various intervals over 2 to 4 hours also provides information on insulin sensitivity; insulin sensitivity can been assessed by calculating insulin area under the curve (AUC$_{insulin}$), the ratio of AUC$_{glucose}$/AUC$_{insulin}$, or by looking at the 2-hour glucose/insulin (G/I) ratio, with a G/I ratio of <1.0 suggestive of insulin resistance.

A CD36 antagonist is also useful for treating or preventing metabolic syndrome, which is characterized by a group of metabolic risk factors in one person. The risk factors include:

Abdominal obesity (excessive fat tissue in and around the abdomen)

Atherogenic dyslipidemia (blood fat disorders—high triglycerides, low HDL cholesterol and high LDL cholesterol—that foster plaque buildups in artery walls)

Elevated blood pressure

Insulin resistance or glucose intolerance (the body can't properly use insulin or blood sugar)

Prothrombotic state (e.g., high fibrinogen or plasminogen activator inhibitor-1 in the blood)

Proinflammatory state (e.g., elevated C-reactive protein in the blood).

People with the metabolic syndrome are at increased risk of coronary heart disease and other diseases related to plaque buildups in artery walls (e.g., stroke and peripheral vascular disease) and type 2 diabetes. Metabolic syndrome has become increasingly common in the United States and worldwide. It is estimated that over 50 million Americans have risk factors indicating metabolic syndrome.

The dominant underlying risk factors for this syndrome appear to be abdominal obesity and insulin resistance. Insulin resistance is a generalized metabolic disorder, in which the body can't use insulin efficiently. This is why the metabolic syndrome is also called the insulin resistance syndrome.

Other conditions associated with the syndrome include physical inactivity, aging, hormonal imbalance and genetic predisposition. Some people are genetically predisposed to insulin resistance. Acquired factors, such as excess body fat and physical inactivity, can elicit insulin resistance and metabolic syndrome in these people. Most people with insulin resistance have abdominal obesity. The biologic mechanisms at the molecular level between insulin resistance and metabolic risk factors are complex and not fully understood.

There are no well-accepted criteria for diagnosing metabolic syndrome. The criteria proposed by the National Cholesterol Education Program (NCEP) Adult Treatment Panel III (ATP III), with minor modifications, are currently recommended and widely used. The American Heart Association and the National Heart, Lung, and Blood Institute recommend that the metabolic syndrome be identified as the presence of three or more of these components:

Elevated waist circumference:
   Men—Equal to or greater than 40 inches (102 cm)
   Women—Equal to or greater than 35 inches (88 cm)
Elevated triglycerides: Equal to or greater than 150 mg/dL
Reduced HDL ("good") cholesterol:
   Men—Less than 40 mg/dL
   Women—Less than 50 mg/dL
Elevated blood pressure: Equal to or greater than 130/85 mm Hg
Elevated fasting glucose Equal to or greater than 100 mg/dL.

In another aspect, the invention is directed to use of a pharmaceutical composition that contains a CD36 antagonist in a pharmaceutically acceptable vehicle (i.e., excipient) for treatment of diabetes or obesity, or to prevent fat accumulation or to promote weight loss, or to increase insulin sensitivity. The pharmaceutical composition can also be formulated together with one or more medications that improve the overall efficacy of the pharmaceutical composition and/or reduce or avoid side effects.

The active ingredient(s) and excipient(s) can be formulated into compositions and dosage forms according to methods known in the art. As described in detail below, the pharmaceutical compositions of the present invention can be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically acceptable" refers herein to those compounds, materials, compositions, and/or dosage forms that are, within the scope of sound medical judgment, suitable for administration to a subject. The phrase "pharmaceutically acceptable excipient" as used herein refers to a pharmaceutically acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic composition for administration to the subject. Each excipient should be "acceptable" in the sense of being compatible with the other ingredients of the formulation and not injurious to the subject.

Some examples of materials which can serve as pharmaceutically acceptable excipients, particularly for liquid forms, include sugars (e.g., lactose, glucose and sucrose); starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; buffering agents; water; isotonic saline; pH buffered solutions; and other non-toxic compatible substances employed in pharmaceutical formulations. If desired, certain sweetening and/or flavoring and/or coloring agents can be added. Other suitable excipients can be found in standard pharmaceutical texts, e.g. in "Remington's Pharmaceutical Sciences", *The Science and Practice of Pharmacy,* 19th Ed. Mack Publishing Company, Easton, Pa., (1995).

Diluents increase the bulk of a solid pharmaceutical composition, and can make a pharmaceutical dosage form that is easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach can be increased by the addition of a disintegrant to the composition. Disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include, for example, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of bacterial adenyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity-enhancing agent to improve the mouthfeel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents, such as sorbitol, saccharin, sodium saccharin, sucrose, aspartame, fructose, mannitol and invert sugar, can be added to improve the taste. Flavoring agents and flavor enhancers can make the dosage form more palatable to the patient. Common flavoring agents and flavor enhancers for pharmaceutical products that can be included in the composition of the present invention include, for example, maltol, vanillin, ethyl vanillin, menthol, citric acid, fumaric acid, ethyl maltol and tartaric acid.

Preservatives and chelating agents, such as alcohol, sodium benzoate, butylated hydroxy toluene, butylated hydroxyanisole and ethylenediamine tetraacetic acid, can be added at levels safe for ingestion to improve storage stability.

According to the present invention, a liquid composition can also contain a buffer such as gluconic acid, lactic acid, citric acid or acetic acid, sodium gluconate, sodium lactate, sodium citrate or sodium acetate. Selection of excipients and the amounts used can be readily determined by the formulation scientist based upon experience and consideration of standard procedures and reference works in the field.

Solid and liquid compositions can also be dyed using any pharmaceutically acceptable colorant to improve their appearance and/or facilitate patient identification of the product and unit dosage level.

The dosage form of the present invention can be a capsule containing the composition, for example, a powdered or granulated solid composition of the invention, within either a hard or soft shell. The shell can be made from gelatin and optionally contain a plasticizer such as glycerin and sorbitol, and an opacifying agent or colorant.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling can include any of the aforementioned blends and granulates that were described with reference to tableting, except that they are not subjected to a final tableting step.

In another aspect, the invention is directed to methods for treatment of diabetes or obesity, or to prevent fat accumulation or to promote weight loss, or to increase insulin sensitivity, by administering to the subject a CD36 inhibiting composition described above. The subject primarily considered herein is a human, although other animals can benefit as well, including mammals, such as dogs, cats, monkeys, cows, and others.

In one embodiment, the composition is administered to the subject in such a manner that the composition does not specifically target particular tissue or cells of the body. In the foregoing embodiment, CD36 is generally inhibited in the subject. In another embodiment, the composition is administered to the subject in such a manner that the composition selectively targets particular tissue or cells. The composition can be made to selectively target particular tissue or cells within the subject by, for example, administering the composition in a localized manner at the site of target tissue or cells (e.g., by injection into target tissue or cells). In an alternative embodiment, the composition can be made to selectively target particular tissue or cells within a subject by administering the composition non-locally or locally, and including in the composition a selective targeting agent that selectively targets certain tissues or certain cells of the subject (e.g., by employing an antibody targeting agent). The tissue being treated can be, for example, tissue of the liver, bone marrow, spleen, skin, lungs, nerves (particularly of the peripheral nervous system), and brain. The end result of the therapy is that the subject experiences, either overall or in specific treated tissue, inhibition of CD36.

As described above, and depending on how the composition is formulated as well as the type of condition to be treated, the composition can be administered orally (e.g., by swallowing or enteral ingestion of tablets, capsules, powders, granules, pastes, solutions, suspensions, drenches, or syrups); parenterally, by, for example, subcutaneous, intramuscular or intravenous injection as; topically, by, for example, applying as a cream, ointment or spray to the skin, internal organs (e.g., lungs), or mucous membranes; or by applying as a pessary, cream or foam, or sublingually; ocularly, transdermally, or nasally.

In order to realize the therapeutic effect of CD36 inhibition, the CD36-inhibiting composition is administered in a therapeutically-effective amount. As is well known in the art, the dosage of the active ingredient(s) significantly depends on such factors as the method of administration, size of the subject, and potential side effects. In different embodiments, depending on these and other factors, a suitable dosage of the active ingredient of the CD36-inhibiting composition can be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Further to the above embodiments, depending on the same and other factors, the composition is administered in the indicated amount by any suitable schedule, e.g., once, twice, or three times a day for a total treatment time of one, two, three, four, or five days, and up to, for example, one, two, three, or four weeks. Alternatively, or in addition, the composition is administered until a desired amount of CD36 inhibition is reached. The desired level of CD36 inhibition can be any level deemed by a professional in the medical arts to be appropriate to achieve.

EXAMPLES

The present description is further illustrated by the following examples, which should not be construed as limiting in any way. The contents of all cited references (including literature references, issued patents, published patent applications as cited throughout this application) are hereby expressly incorporated by reference.

Example 1

Chronic SAB treatment in hyperlipidemic ApoE KO (AKO) mice reduces weight gain and visceral fat accumulation. ApoE KO mice spontaneously exhibit a hyperlipidemic phenotype. Feeding a high fat diet to the ApoE KO mice for 8 weeks increases plasma cholesterol levels approximately 5 fold (Kim et al., 2008). Six week old male ApoE KO (HL AKO) mice were fed a high fat diet for 8 weeks with or without SAB (100 mg/kg, subcutaneously every other day). Weekly body weight measurement showed that SAB treatment significantly reduced the rate of weight gain. The difference in weight between the groups was apparent by the 3rd week of treatment (FIG. 1A). Compared to vehicle treated ApoE KO mice, SAB-treated mice were 17% leaner (FIG. 1A) and the abdominal fat accumulation was either minimal or absent (FIG. 1B). In addition, SAB treatment significantly reduced plasma cholesterol levels (FIG. 1H) and fat deposition in the liver (FIG. 1I). Thus, SAB reduces body weight and fat accumulation, particularly visceral/abdominal fat accumulation and liver fat deposits, and also lowers plasma cholesterol. This suggests that CD36 antagonists such as SAB can be beneficial in treatment and prevention of metabolic syndrome and other metabolic disorders.

Example 2

SAB treatment improves insulin sensitivity. Fasting blood glucose levels were similar in SAB-treated and control mice at zero, four, and eight weeks of treatment (FIG. 1C). However, when mice were challenged with glucose tolerance test (an intraperitoneal injection of 1.5 mg glucose/kg), blood glucose was cleared much faster in SAB-treated mice (45 minutes after challenge, initial blood glucose spike reduced by 75%) relative to vehicle-treated mice (45 minutes after challenge, initial spike in blood glucose reduced by less than 10%; FIG. 1D). Quantification of this glucose tolerance test showed a significant reduction of $AUC_{glucose}$ (glucose area under the curve) in SAB-treated mice (FIG. 1E), indicating SAB treatment substantially improves insulin sensitivity and assists in lowering blood glucose levels following blood glucose elevation. This suggests that treatment with CD36 inhibitors such as SAB can be beneficial for treatment and prevention of diabetes, pre-diabetes, and other disorders characterized by abnormal blood insulin and/or glucose levels.

Example 3

SAB treatment reduces CD36 expression in peritoneal macrophages. Since CD36 is expressed in monocytes and macrophages, CD36 gene expression was compared in peritoneal macrophages and the spleen, a peripheral organ that serves as a reservoir of monocytes, from vehicle and SAB-treated mice. CD36 mRNA levels were reduced in both peritoneal and spleen macrophages of SAB-treated mice (FIG. 1F). Because the presence of ligands increases CD36 gene expression in a feed forward manner, it is hypothesized that SAB acts to antagonize ligand-receptor interactions, resulting in the reduction of CD36 gene expression. Preliminary analysis of lipid content in the aorta and extended vessels also showed a trend toward lipid content reduction in the vessels obtained from SAB-treated mice (FIG. 1G). Thus, CD36 antagonists such as SAB are useful in reducing CD36 function, leading to therapeutically useful results such as reduced plasma lipid and cholesterol levels.

Example 4

Visceral fat weight in high fat fed ApoE KO mice treated with either vehicle or SAB (100 mg/kg) for 8 weeks. 100 mg/kg SAB or vehicle (veh) was injected every other day by subcutaneous injection. n=8-10 mice/group, ***, p<0.001. Reduction in abdominal fat was evident on physical inspection (FIG. 2A). SAB reduced visceral fat weight by 60% (32 mg average visceral fat weight in SAB treated mice versus 81 mg average visceral fat weight in controls; FIG. 2B). This provides further evidence that CD36 antagonists can reduce fat accumulation, particularly visceral fat accumulation.

Example 5

Figure 3:
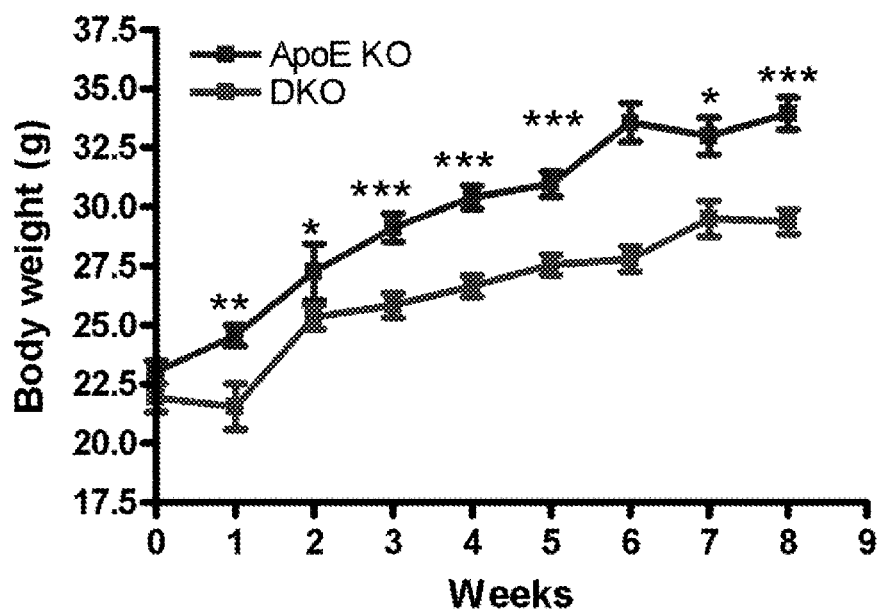
FIG. 3. CD36 deficiency reduces body weight of ApoE KO mice. Six week old ApoE KO and ApoE/CD36 double KO (DKO) mice were fed a high fat diet for 8 weeks and their body weight gain was measured weekly. Body weight gain in CD36 deficient ApoE KO mice was significantly reduced (weight gain=34%) compared to weight gain in ApoE KO mice with wild-type CD36 (weight gain=41%).

CD36 deficiency reduces body weight of ApoE KO mice. Six week old ApoE KO and ApoE/CD36 double KO (DKO) mice were fed a high fat diet for 8 weeks and their body weight gain was measured weekly. There was a significant reduction in body weight gain (approximately 14%) in CD36 deficient ApoE KO mice (FIG. 3). These data are consistent with the result of pharmacological inhibition by Salvianolic acid B (SAB) shown in FIG. 1A. This provides more evidence that CD36 antagonists are useful for reducing body weight and ameliorating conditions associated with excess fat and body weight, such as metabolic syndrome, in individuals eating a high fat diet.

Example 6

Figure 4:
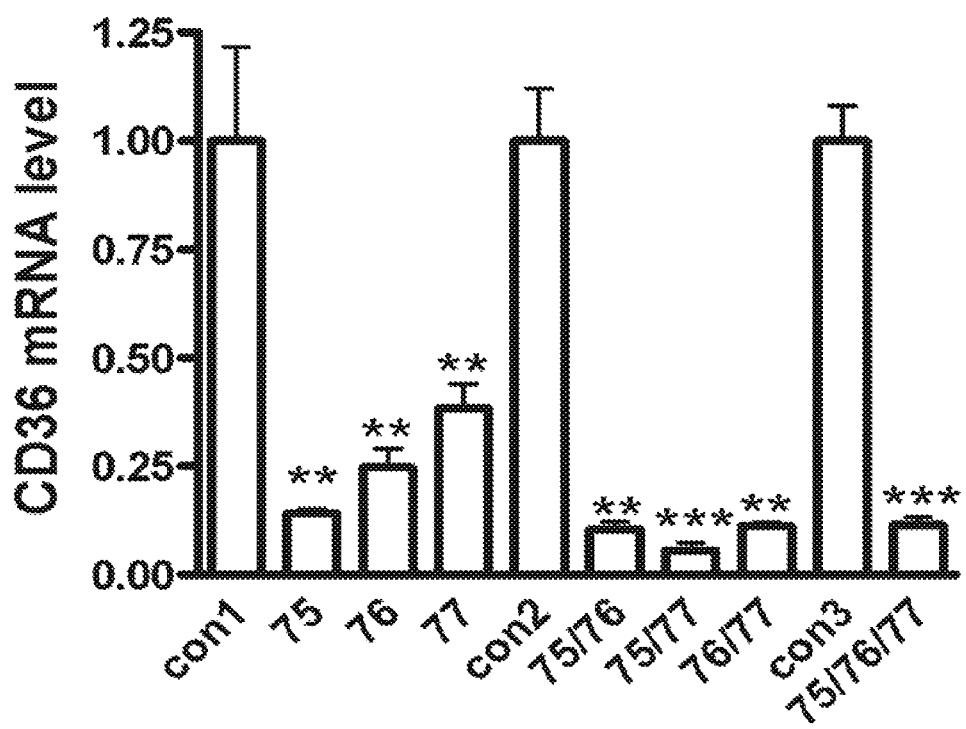
FIG. 4. Efficacy of CD36 siRNA. 20 nM siRNA either singly or in combination were transfected in C8-D1A cells. CD36 mRNA levels were measured 24h later. N=4. Negative controls were adjusted to the amount of siRNA. p<0.01, *p<0.001 vs correponding control.

CD36 was inhibited using an RNAi technique. 20 nM siRNA either singly or in combination were transfected in C8-D1A cells. CD36 mRNA levels were measured 24h later. N=4. Negative controls were adjusted to the amount of siRNA. p<0.01, *p<0.001 vs correponding control. The study showed all siRNAs for CD36 siRNA [MSS202775 (from exon9), MSS202776 (exon7), MSS202777 (exon11)] reduced CD36 gene expression significantly, with siRNA 75 being the most effective (FIG. 4). These results provide further evidence that CD36 antagonism can be effected at multiple levels, including direct inhibition and prevention of CD36 expression.

The siRNAs used in these experiments are:

```
siRNA No. MSS202775:
                                       (SEQ ID NO: 1)
5'-UAG CUU GGC CAA UAG GAC AAA UUC C-3';

(SEQ ID NO: 2)
5'-GGA AUU UGU CCU AUU GGC CAA GCU A-3'.

siRNA No. MSS202776:
                                       (SEQ ID NO: 3)
5'-CUU GUU UGG AAC ACA GAA GAC UUG G-3';

(SEQ ID NO: 4)
5'-CCA AGU CUU CUA UGU UCC AAA CAA G-3'.

siRNA No. MSS202777:
                                       (SEQ ID NO: 5)
5'-ACA CCA UAA GAU GUA CAG UUA UUG G-3';

(SEQ ID NO: 6)
5'-CCA AUA ACU GUA CAU CUU AUG GUG U-3'
```

Example 7

Figures 5A, 5B, 5C, 5D, 5E, 5F:
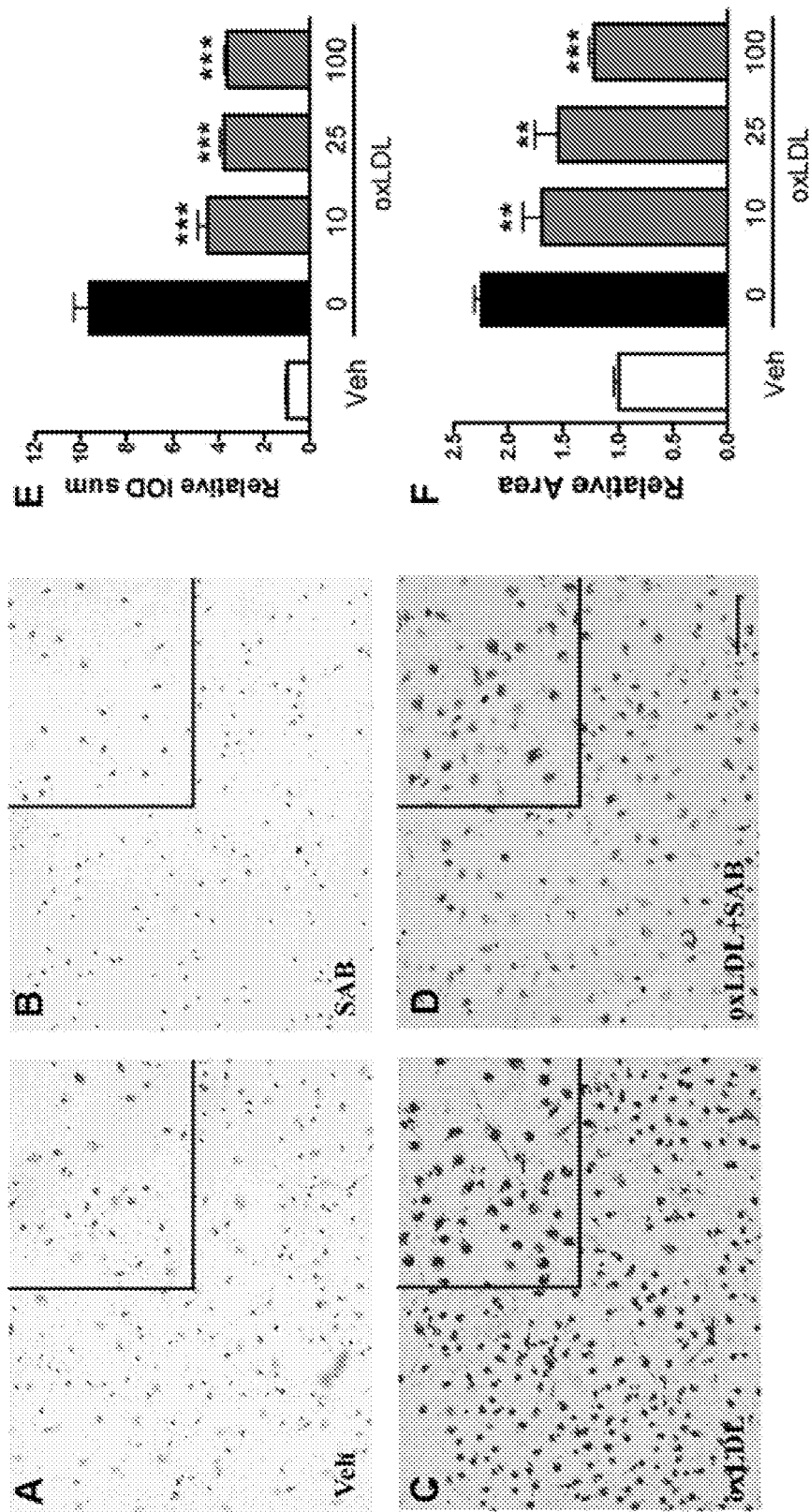
FIG. 5. Effects of SAB on lipid accumulation in ApoE KO mouse macrophages. Primary macrophages were seeded in 4 chamber slides and then incubated with 20 µg/ml oxLDL and/or different concentrations of SAB for 48 h. (A-D) Lipids were stained with oil red O and examined by microscopy; representative images are shown. (A), vehicle only; (B), 25 µM SAB treatment; (C), 20 µg/ml oxLDL; (D), 20 µg/ml oxLDL+25 µM SAB. Scale bar, 50 µm; higher magnification micrographs of oil red O stains were shown in upper-right of each picture. (E-F), Quantification for foam cell assay in primary macrophage. White bar, macrophages incubated with vehicle only (no oxLDL or SAB); black bar, incubated with 20 µg/ml oxLDL; grey bars, incubated with 20 µg/ml oxLDL plus 10, 25 or 100 µM SAB (SAB concentration listed below each bar); (E), Degree of lipid accumulation measured as intensity of integrated optical density; (F), Foam cell average area compared to average area of control macrophages incubated with vehicle. Control (vehicle-treated) average individual macrophage cell size/ area was normalized as 1; macrophages treated with oxLDL show increased individual relative cell area resulting from lipid internalization (black bar); SAB treatment (grey bars) reduced lipid internalization and relative cell size/area. n=3-6 cells/group. ,*p<0.01, 0.001 compared with no oxLDL(0).

SAB reduces lipid accumulation in ApoE KO mouse macrophages. Primary macrophages were isolated from ApoE KO mice and incubated with oxidized low density lipoproteins (oxLDL) and/or different concentrations of SAB for 48 h, then stained for lipid accumulation. Macrophages incubated with oxLDL showed extensive staining, consistent with significant lipid accumulation (FIG. 5C). In contrast, macrophages treated with oxLDL plus SAB showed significantly reduced lipid accumulation (FIG. 5D). Thus, CD36 antagonists can prevent accumulation of fat and lipids in cells subject to lipid-rich environments.

Example 8

SAB reduces lipid accumulation and foam cell formation. Primary macrophages cultured from ApoE KO mice show a low intensity of optical density (IOD) commensurate with small cellular area (FIGS. 5E and 5F, white bar). Incubation of these macrophages with oxLDL results in a large increase in IOD, consistent with an increase in relative cellular area resulting from extensive lipid accumulation (FIGS. 5E and 5F, black bar). However, macrophages incubated with oxLDL plus 10, 25 or 100 µM SAB (FIGS. 5E and 5F, grey bars; SAB concentration listed below each bar) show significantly reduced IOD and relative cell area compared to macrophages treated with oxLDL alone. This indicates that CD36 antagonists reduce cellular lipid internalization, a marker of foam cell formation and atherosclerotic development.

What is claimed is:

1. A method to reduce body weight in a subject in need thereof comprising administering to said subject an effective amount of a CD36 antagonist selected from the group consisting of salvianolic acid B (SAB), and sodium danshensu (DSS).

2. The method of claim 1 wherein said CD36 antagonist is SAB.

3. The method of claim 1 wherein said subject is obese.

4. The method of claim 1 wherein said subject is overweight.

5. A method to inhibit fat accumulation in a subject in need thereof comprising administering to said subject an effective amount of a CD36 antagonist selected from the group consisting of salvianolic acid B (SAB), and sodium danshensu (DSS).

6. The method of claim 5 wherein said fat is visceral fat.

7. The method of claim 5 wherein said small CD36 antagonist is SAB.

8. The method of claim 5 wherein said subject is obese.

9. The method of claim 5 wherein said subject is overweight.

10. A method to increase insulin sensitivity or glucose tolerance in a subject in need thereof comprising administering to said subject an effective amount of a CD36 antagonist selected from the group consisting of salvianolic acid B (SAB), and sodium danshensu (DSS).

11. the method of claim 10 wherein said CD36 antagonist is SAB.

12. The method of claim 10 wherein said subject has diabetes.

13. The method of claim 12 wherein said subject has Diabetes Type II.

14. The method of claim 12 wherein said subject has gestational diabetes.

15. The method of claim 12 wherein said subject has pre-diabetes.

16. A method to treat or prevent diabetes or pre-diabetes in a subject in need thereof comprising administering to said subject an effective amount of a CD36 antagonist selected from the group consisting of salvianolic acid B (SAB), and sodium danshensu (DSS).

17. The method of claim 16 wherein said CD36 antagonist is SAB.

18. The method of claim 16 wherein said diabetes is Diabetes Type II.

19. The method of claim 16 wherein said diabetes is gestational diabetes.

* * * * *

SEQUENCE LISTING

```
<160> NUMBER OF SEQ ID NOS: 6

<210> SEQ ID NO 1
<211> LENGTH: 25
<212> TYPE: RNA
<213> ORGANISM: Artificial Sequence
<220> FEATURE:
<223> OTHER INFORMATION: synthetic siRNA

<400> SEQUENCE: 1
uagcuuggcc aauaggacaa auucc                                         25

<210> SEQ ID NO 2
<211> LENGTH: 25
<212> TYPE: RNA
<213> ORGANISM: Artificial Sequence
<220> FEATURE:
<223> OTHER INFORMATION: synthetic siRNA

<400> SEQUENCE: 2
ggaauuuguc cuauuggcca agcua                                         25

<210> SEQ ID NO 3
<211> LENGTH: 25
<212> TYPE: RNA
<213> ORGANISM: Artificial Sequence
<220> FEATURE:
<223> OTHER INFORMATION: synthetic siRNA
```

```
-continued

<400> SEQUENCE: 3
cuuguuugga acacagaaga cuugg                                        25

<210> SEQ ID NO 4
<211> LENGTH: 25
<212> TYPE: RNA
<213> ORGANISM: Artificial Sequence
<220> FEATURE:
<223> OTHER INFORMATION: synthetic siRNA

<400> SEQUENCE: 4
ccaagucuuc uauguuccaa acaag                                        25

<210> SEQ ID NO 5
<211> LENGTH: 25
<212> TYPE: RNA
<213> ORGANISM: Artificial Sequence
<220> FEATURE:
<223> OTHER INFORMATION: synthetic siRNA

<400> SEQUENCE: 5
acaccauaag auguacaguu auugg                                        25

<210> SEQ ID NO 6
<211> LENGTH: 25
<212> TYPE: RNA
<213> ORGANISM: Artificial Sequence
<220> FEATURE:
<223> OTHER INFORMATION: synthetic siRNA

<400> SEQUENCE: 6
ccaauaacug uacaucuuau ggugu                                        25
```